United States Patent [19]

Arnost et al.

[11] Patent Number: 4,900,686

[45] Date of Patent: Feb. 13, 1990

[54] FLUORESCENT CONJUGATES AND BIOLOGICAL DIAGNOSTIC ASSAY

[75] Inventors: Michael J. Arnost, Andover; Frank A. Meneghini, Arlington; Paul S. Palumbo, West Newton; Stephen G. Stroud, Medford, all of Mass.

[73] Assignee: Polaroid Corporation, Cambridge, Mass.

[21] Appl. No.: 34,225

[22] Filed: Apr. 2, 1987

[51] Int. Cl.[4] ............................................ G01N 33/533
[52] U.S. Cl. ................................. 436/546; 435/6; 435/805; 435/810; 436/501; 436/518; 436/536; 436/547; 436/800; 436/805; 436/808; 536/27; 536/28; 530/388; 530/389; 546/48
[58] Field of Search ............................ 435/6, 805, 810; 436/501, 512, 518, 536, 546, 547, 800, 805, 808; 536/27; 530/389, 802; 546/48

[56] References Cited

U.S. PATENT DOCUMENTS

| | | | |
|---|---|---|---|
| 3,822,270 | 7/1974 | Reynolds | 546/48 |
| 3,932,415 | 1/1976 | Reynolds | 546/48 |
| 4,005,092 | 1/1977 | Reynolds | 546/48 |
| 4,351,760 | 9/1982 | Khanna et al. | 436/546 |
| 4,463,099 | 7/1984 | Baroncelli | 435/546 |
| 4,481,136 | 11/1984 | Khanna et al. | 436/546 |
| 4,588,697 | 5/1986 | Khanna et al. | 436/546 |
| 4,622,400 | 11/1986 | Hammond | 546/48 |

*Primary Examiner*—Sam Rosen
*Attorney, Agent, or Firm*—Gaetano D. Maccarone

[57] ABSTRACT

There are provided novel fluorescent conjugates comprising a rhodamine dye moiety and a biologically active moiety. In addition, there are provided methods for determining an analyte in a biological fluid.

30 Claims, No Drawings

FLUORESCENT CONJUGATES AND BIOLOGICAL DIAGNOSTIC ASSAY

BACKGROUND OF THE INVENTION

It is known in the biological diagnostic assay field to utilize conjugates of biologically active moieties with a detectable, signal-generating dye moiety which may be, for example, a moiety which emits electromagnetic radiation, e.g., a fluorescent, chemiluminescent or bioluminescent moiety. The biologically active moiety may be: a DNA probe, e.g., a labeled DNA probe of the type used in detecting complementary DNA sequences; an enzyme; an enzyme inhibitor; an antigen; an antibody; a hapten, etc.

In recent years much attention has been focused on labeled-reagent immunoassays for the detection of body fluid components such as antigens, hormones, infectious agents, serum antibodies and the like. Consequently, the patent literature includes many disclosures of various assays involving a labeled-reagent reaction between antigens and antibodies to provide a detectable signal which may be a change in color, emission of electromagnetic radiation, etc. These assays involve an immunological interaction between a ligand and an antiligand wherein at least one of the two reactants contains a substance or a precursor of a substance which can provide the detectable signal as a function of the immunological ligand-antiligand interaction.

One class of labels commonly used in such assays are fluorescent dyes or fluorophores. Both heterogeneous and homogeneous specific binding assays employing fluorescent-labeled conjugates are well known in the art. In general, it is desirable that fluorescent labels for use in such assays have a relatively long emission wavelength, e.g., above 500 mm. In addition, it is desirable that the labels have a large Stokes shift, be stable under the assay conditions, be relatively free of non-specific interference both from materials in solution and the moiety to which the label is conjugated and provide high quantum yields.

The present invention relates to novel fluorescent conjugates comprising a rhodamine dye moiety linked to a biologically active moiety and their use in biological diagnostic assay elements and processes.

It is therefore an object of this invention to provide novel fluorescent conjugates which include a biologically active moiety and a fluorescent dye moiety.

A further object is to provide biological diagnostic assay elements and processes.

BRIEF SUMMARY OF THE INVENTION

These and other objects and advantages are accomplished in accordance with the invention by providing novel fluorescent conjugates which are represented by the formula

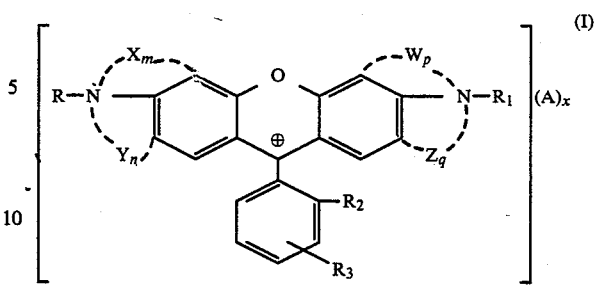

wherein
W, X, Y and Z are the same or different and each is represented by $-(CH_2)_a(CHR_4)(CH_2)_b-$;
a and b each independently is an integer of from 0 to 4, provided that the sum of a+b is an integer of from 1 to 4;
m and n each is 0 or 1, provided that one of m and n is 0 and one of m and n is 1;
p and q each is 0 or 1, provided that one of p and q is 0 and one of p and q is 1;
R, $R_1$, $R_3$ and $R_4$ each independently is hydrogen, a substituent including a hydrophilic group such as, for example, a carboxylic acid, a polyalcohol, a sulfonic acid or the like, or a substituent including a biologically active moiety such as an antigen, an antibody or the like;
$R_2$ is $-CO_2^\ominus$, $SO_3^\ominus$; or a substituent including a biologically active moiety such as those described above;
provided that at least one of R, $R_1$, $R_2$, $R_3$ and $R_4$ is a substituent including a biologically active moiety;
A is a counterion or counterions to balance the charges produced by the conjugate moiety; and x is 0 or 1.

It will be understood that where the conjugate moiety is neutral overall no counterion is needed. The counterion, A, may be any biologically acceptable anion or cation such as, for example, chloride, sulfate, diphenylphosphate, trifluoroacetate, trimethylammonium, sodium, potassium, calcium and the like. It will also be understood that when the conjugate moiety has a net overall charge greater than one, the charges may be balanced by one or more counterions. For example, where the conjugate moiety has a net overall charge of +2, these charges can be balanced by two chloride ions or one sulfate ion.

It should be noted that by "hydrophilic group", as used in the specification and claims herein, is meant a group which will improve the solubility of the molecule in water. Typical suitable hydrophilic groups which may be incorporated in the novel fluorescent compounds of the invention include: carboxylic acids (—COOH); polyethers such as those represented by $-(OCH_2CH_2)_c-O$ Et where c is an integer of from 1 to 20 such as polyethylene oxide; polyalcohols which are represented by $-CH_2-(CHOH)_d-CH_2OH$ where d is an integer of from 1 to 20; primary, secondary or tertiary amines which are represented by $-NR_5R_6$ where $R_5$ and $R_6$ each independently is hydrogen, alkyl, preferably having from 1 to 6 carbon atoms, aryl such as phenyl or polyamines such as

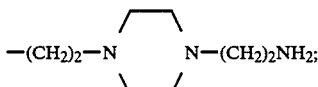

sulfonic acids (—$SO_3H$); phosphonic acids or esters which are represented by —$(CH_2)_e$—$PO(OR_7)(OR_8)$ where e is an integer of from 1 to 8 and $R_7$ and $R_8$ each independently is hydrogen, alkyl, preferably having from 1 to 6 carbon atoms or aryl such as phenyl; phosphates represented by —$(CH_2)_e$—$OPO(OH)_2$; phosphate esters represented by —$(CH_2)_e$—$OPO(OH)(OR_9)$ where $R_9$ is alkyl, preferably having from 1 to 6 carbon atoms or aryl such as phenyl; phosphinic acids represented by —$(CH_2)_e$—$PO(OH)R_{10}$ where $R_{10}$ is alkyl, preferably having from 1 to 6 carbon atoms; boronic acids which are represented by —$R_{11}$—$B(OH)_2$ where $R_{11}$ is —$(CH_2)_e$— or aryl such as phenyl; and borinic acids represented by —$R_{11}$—$B(OH)R_{10}$. As will be shown in more detail below, the compounds of the invention may include one or more of the same hydrophilic groups or they may include more than one different type of hydrophilic group.

The novel fluorescent conjugates within Formula I have emission maxima which are above 500 nm, typically in the range of from about 500 nm to about 650 nm.

Generally, the novel conjugates of the invention include at least one biologically active moiety which can be attached directly to the dye chromophore or which can be attached to the dye chromophore through a divalent achromophoric linking group. By the term "achromophoric linking group" is meant one which does not cause any appreciable shift in the spectral absorption characteristics of the dye moiety. Thus, in Formula I, where any of R, $R_1$, $R_2$, $R_3$ or $R_4$ is a substituent including a biologically active moiety, such substituent may include a divalent achromophoric linking group to link the dye moiety to the biologically active moiety. Such a linkage should be non-conjugated.

The biologically active moiety may be any such as, for example, an antigen, an antibody, a hapten, a DNA probe, an Fab fragment, etc.

Typical functional groups which are useful as coupling groups which can be attached to the dye molecule, and the substituents of the biologically active moiety with which such coupling groups are reactable to provide the achromophoric linking group within the labeled conjugates, are:

| COUPLING GROUP | SUBSTITUENT OF BIOLOGICALLY ACTIVE GROUP |
|---|---|
| N—hydroxysuccinimide esters | amino groups (α-amino, lysine) |
| Imidoester | amino groups |
| Aldehydes | amino groups |
| Mixed anhydrides | nucleophilic groups |
| Isothiocyanates | nucleophilic groups |
| 2,4-dichloro-5-triazine | nucleophilic groups |
| Diazonium salts | tryptamine, histamine |
| Bromoacetyl | histamine, SH |
| Maleimido | SH |
| Activated disulfide bonds (e.g. 2-pyridyldisulfides) | SH |

Many other linking groups may be incorporated into the conjugates of the invention. For example, the hydrophilic groups mentioned above are substantially achromophoric and certain of these can be derivatized and utilized as suitable linking groups. For example, an —$NH_2$ group can be converted to an amide as a result of attaching the biologically active moiety (BIO) to it, i.e., —NHCO—BIO. Further, in another embodiment a hydrophilic group may be attached to the linking group. For example, in the case of a primary amine, one of the hydrogen atoms is replaced by a biologically active moiety attached to it as described above and the other hydrogen atom can be replaced by a hydrophilic group such as, for example, —$(CH_2)_2PO_3H_2$. Thus, it will be appreciated that the linking group, while serving as the means for attaching the dye moiety to the biologically active moiety, can also have a hydrophilic group attached to it. In addition, the linking group may also function as a hydrophilic group such as, for example, in the case of —NH—BIO and —$PO_2(OH)$—BIO.

The labeled fluorescent conjugates of the invention are useful in various applications including diagnostic assays which are based on an energy transfer mechanism to activate the fluorescent label. The fluorescent dye moieties typically have maximum absorption, $\lambda$ max, of from about 500 nm to about 650 nm, exhibit Stokes shifts of about 15–20 nm and have high quantum yields of about 0.7–0.8. These dye moieties advantageously offer a number of positions of attachment for biologically active moieties and/or solubilizing groups. The presence of such solubilizing groups can help to avoid undesirable nonspecific binding of the conjugates to components present in biological fluids such as, for example, plasma proteins.

DESCRIPTION OF THE PREFERRED EMBODIMENT

A preferred class of conjugates according to the invention is represented by the formula

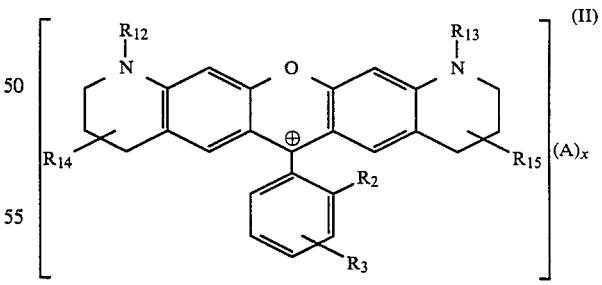

where $R_{12}$, $R_{13}$, $R_{14}$ and $R_{15}$ may be the same or different and each independently is hydrogen, a substituent including a hydrophilic group such as any of those described above, or a substituent including a biologically active moiety such as any of those described above; and $R_2$, $R_3$, A and x are as previously defined.

Another preferred class of conjugates according to the invention is represented by the formula

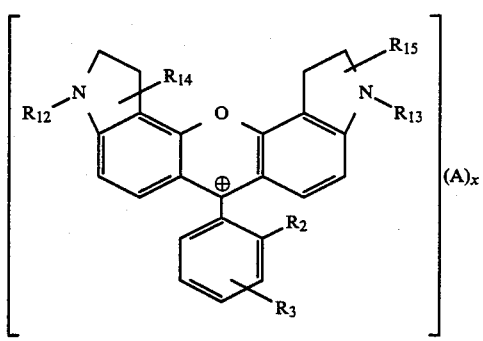

wherein $R_2$, $R_3$, $R_{12}$, $R_{13}$, $R_{14}$, $R_{15}$, A and x are as previously defined.

As stated previously, in the conjugates of the invention the biologically active moiety may be attached to the fluorescent dye moiety at various positions. In a preferred embodiment the biologically active moiety is included within substituent $R_2$ (Formula I). The biologically active moiety is preferably attached through a linkage which is a carboxamido piperazinyl derivative represented by the formula

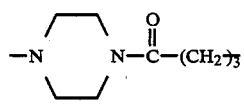

Thus, in this preferred embodiment $R_2$ is represented by

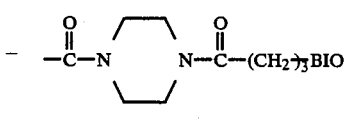

or

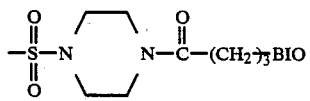

The attachment of the biologically active moiety to the linkage may be through any appropriate position on that moiety. For example, where the biologically active moiety is theophylline it may be attached to the linkage through the 3- or 8- positions.

The labeled conjugates of the invention may be used in any of many applications such as, for example, in diagnostic assays such as competitive binding assays or immunoassays or in immune response reactions employing labeled reagents. In a preferred embodiment, the conjugates are employed in drug monitoring applications such as for theophylline, phenytoin, etc. or in hormone monitoring applications such as thyroxine (T4). The particular assays in which the conjugates of the invention find utility are well known, e.g., immunometric assays, competitive binding assays, etc. and therefore extensive discussion of such assays is not required here. In such known diagnostic tests, or assays, a biological reaction or interaction results in the generation of a detectable signal. For instance, in a typical immunoassay carried out in a multilayer assay element, an analyte—containing sample comprising a body fluid such as serum or whole blood is applied to a surface of the element. The fluid is typically passed through a filtering medium to remove interfering species and/or cells and then diffuses to a layer containing the labeled biologically active conjugate to produce an immunological reaction or interaction in accordance with the particular system of the assay element and this reaction or interaction in turn generates a detectable signal which is a function of the analyte in the sample fluid. The signal so generated may in less sophisticated systems provide only a qualitative determination of the presence of analyte or, in more sophisticated systems, it may provide a semi-quantitative measurement of the analyte. In such a system, the biologically active conjugate containing the detectable signal - generating moiety may be a so-called label-protein conjugate, i.e., a protein such as an antigen, antibody or Fab fragment "labeled" with, or containing, the dye moiety.

A typical multilayer assay element according to the invention comprises a support layer, which may be transparent, carrying at least one reagent layer in which there is provided the labeled conjugate of the invention. Also, in the reagent layer(s) there is provided any other reagent which is necessary for the particular signal generating system being exploited for the particular assay. These elements may also include other layers to provide various functions which are known in the art such as, for example: a layer to receive the sample and provide an even distribution of the sample components to the underlying reagent layer(s); a light-blocking, or screen, layer to assist in the detection of the signal by separating the layer in which the signal generating species is located from other layers of the element thus preventing undesirable interference with the detection of the signal; etc.

The conjugates of the invention may also be used for fluorescent staining of cells. The cells may then be observed under a microscope, the presence of the fluorescent conjugate being indicative of the presence of a specific determinant site. Further, the conjugates may be used for the deletion, separation or other application in a fluorescent activated cell sorter.

The conjugates of the invention may be prepared by reactions which are known to those skilled in the art and these will be apparent from the specific examples provided below herein. Accordingly, extensive discussion of such processes is not required here.

The invention will now be described further in detail with respect to specific preferred embodiments by way of Examples, it being understood that these are intended to be illustrative only and the invention is not limited to the specific materials, compositions or processes described therein.

EXAMPLE I

A mixture of 1.9 g (13.0 mmole) of 7-hydroxyquinoline and 100 mg $Pt_2O$ in 75 ml of 95% ethanol was hydrogenated overnight. The mixture was suction filtered through diatomaceous earth and the filtrate evaporated under reduced pressure. The resulting reddish-brown oil slowly crystallized to afford a quantitative yield of

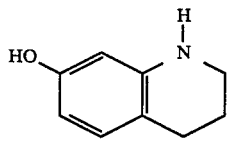

which was stored in the dark under nitrogen.

'H NMR (CDCl$_3$): δ 1.85 (quint., 2H, J=6 Hz), 2.65 (t, 2H, J=6 Hz); 3.23 (t, 2H, 6 Hz); 4.65 (b.s., 2H), 5.95 (d, 1H, J=3 Hz); 6.1 (dd, 1H, J$_1$=90 Hz, J$_2$=3 Hz), 6.75 (d, 1H, J=9 Hz). M.S. (M+149).

The crude product (VII) (28 mmole) was combined neat in a dry flask with 4.16 g (28 mmole) of phthalic anhydride and 1.9 g (14 mmole) of fused ZnCl$_2$ and the resulting mixture was heated in an oil bath at 150° C. under nitrogen for 2 hours. The solid mass was cooled to room temperature, pulverized and extracted with warm water and suction filtered. The resulting red solid was taken up in 250 ml of 18% aq. HCl, warmed on a steam bath and several ml of conc. HCl added to reach solubility. The solution was slowly cooled to room temperature and then stored in a freezer for 2 days. The resulting crystalline product was suction filtered, washed with excess 1N HCl and dried under vacuum to give 2.65 g (42% yield) of

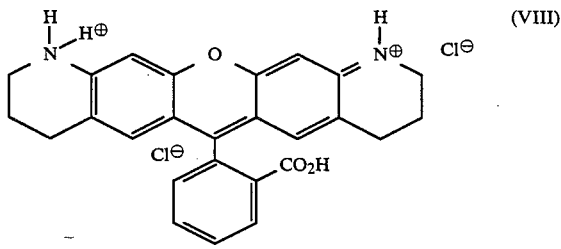

as a purple powder. Titration with potassium-t-butoxide suggested that the product was a bis-HCl salt (M+410 free base).

Potassium-t-butoxide (1.56 g, 13.9 mmole) was added in one portion to a stirred solution of 2.0 g of the previous product (VIII) in 200 ml of dry DMF at 0°–5° C. under nitrogen. A cyan color formed and subsequently dissipated. (Note: subsequently it was found to be more convenient to add the potassium-t-butoxide to a point where the cyan color persists and then add one more equivalent). Another 0.5 g (4.5 mmole) of potassium-t-butoxide was added and the resulting cyan solution stirred for 45 minutes. To this solution there was added, dropwise over a 5 minute period, a solution of 2.2 ml (13.4 mmole) t-butylbromoacetate in 10 ml DMF and the resulting mixture warmed to room temperature. The solvent was then removed under high vacuum followed by taking up the residue in CH$_2$Cl$_2$, filtering through diatomaceous earth and evaporating the filtrate. The product was purified by chromatography on silica gel using 10% CH$_3$OH/CH$_2$Cl$_2$ as the eluent to give 2.0 g (70% yield) of

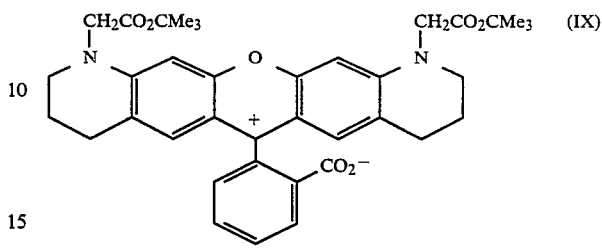

as a magenta powder.

'H NMR (CDCl$_3$): 1.5 (s, 18H), 1.9 (m, 4H), 2.55 (t, 4H, J=6 Hz), 3.4 (t, 4H, J=6 Hz), 3.4 (t, 4H, J=6 Hz), 3.9 (bs., 4H), 6.23 (s,2 H), 6.34 (s, 2H), 7.1–7.2 (m, 1H), 7.5–7.75 (m, 2H), 8.0–8.2 (m, 1H).

A mixture of 370 mg (0.58 mmole) of (IX) and 193 mg (0.58 mmole) of

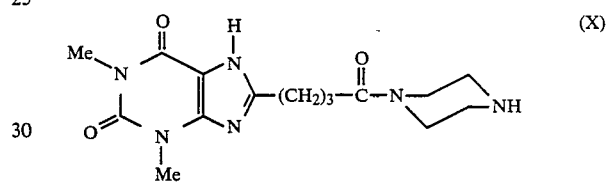

(which was made from the corresponding 8-carboxypropyl theophylline and piperazine via trimethylacetyl mixed anhydride coupling) in 10 ml DMF was cooled to −30° C. Diphenylphosphoryl azide (160 μl, 0.75 mmole) was added to the stirred solution under nitrogen and the bath allowed to warm slowly to room temperature. After 4 days the solution was poured into excess ethyl ether, the liquid decanted from the oil and the oil chromatographed on silica gel using 10–15% CH$_3$OH/CH$_2$Cl$_2$ to give 421 mg (61% yield) of

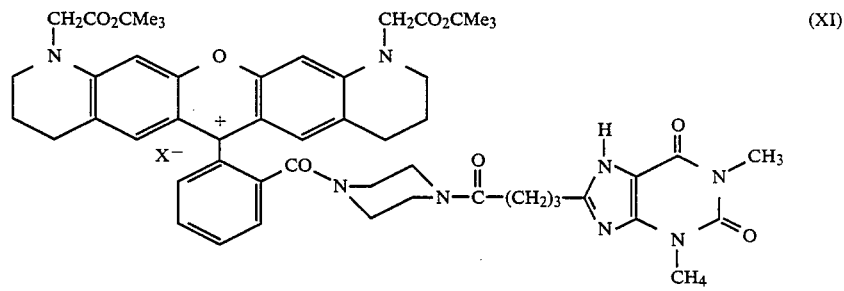

as the diphenylphosphate salt (X=(PHO)$_2$PO$_2$−); (m/e=956 FAB+).

'H NMR (CDCl$_3$) was complex but consistent with the structure of the product.

A solution of 421 mg (0.35 mmole) of (XI) in 10 ml CH$_2$Cl$_2$ was cooled to about 5° C. and treated with 2 ml of trifluoroacetic acid. The resulting mixture was stirred under nitrogen for 30 minutes and then at room temperature overnight. The product was isolated by evaporation of the solvent and purified by chromatography on silica gel with 15%–30% CH$_3$OH/10%

AcOH/CH2Cl2 as the eluent to give the desired conjugate

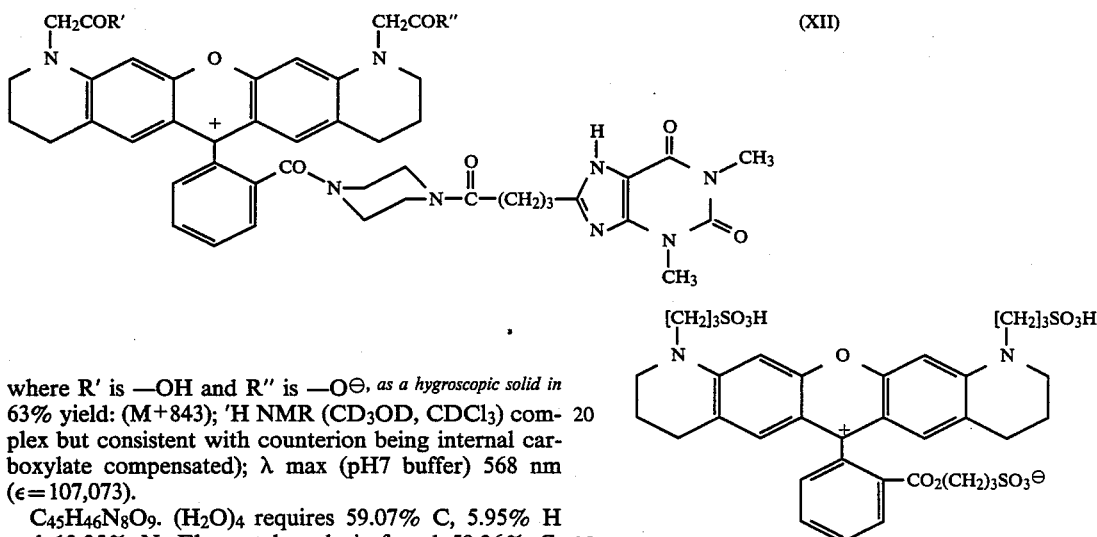

where R' is —OH and R" is —O⊖, *as a hygroscopic solid in* 63% yield: (M+843); 'H NMR (CD3OD, CDCl3) complex but consistent with counterion being internal carboxylate compensated); λ max (pH7 buffer) 568 nm (ε=107,073).

C45H46N8O9·(H2O)4 requires 59.07% C, 5.95% H and 12.25% N. Elemental analysis found 59.26% C, 5.71% H and 12.25% N.

EXAMPLE II

Conjugates XIII (XII where R' is —NH(CH2)2SO3H) and R" is —NH(CH2)2SO3⊖) and XIV (XII where R'=R" and each is —N(CH3)CH2(CHOH)4CH2OH) were synthesized from XII via diphenylphosphoryl azide (DPPA) coupling with taurine and N-methyl-d-glucamine, respectively. Thus, 1 mmole of XII was combined with 3 mmoles of taurine (or 3 mmoles of N-methyl-d-glucamine) and 5 mmoles of triethylamine in the case of taurine (or 2 mmoles in the case of N-methyl-d-glucamine) in ½ ml of dry DMF. To the cooled solutions (−30° C.) there was added 3 mmoles DPPA in one portion, the bath slowly warmed to room temperature and stirred overnight. The products were isolated by evaporation under vacuum and purified by reverse phase chromatography.

Conjugate XIII exhibited λ max (pH7 buffer) 558 nm (ε=74,900). Conjugate XIV exhibited λ max (pH7 buffer) 555 nm (ε=60,300).

EXAMPLE III

To a flamed/N2 cooled 100 ml round bottom flask equipped with an inlet for N2 atmosphere there was added 2.0 g (4.1×10−3 mole) of bis rhodamine HCl salt (VIII) along with 50 ml of dry DMSO (48 hours over 3A sieves). The flask was immersed in a water bath at ambient temperature and then 1.89 g (1.68×10−2 mole) of t-butoxide potassium salt were added in one portion with stirring. The red-violet colored reaction mixture was stirred for 2 hours at ambient temperature. Propane sultone (2.54 g, 2.08 ×10−2 mole) was added in one portion and the reaction mixture stirred for an additional 14 hours at ambient temperature. The crude reaction mixture was evaporated under high vacuum and the resulting solid was triturated with CH3CN and then with ethyl ether prior to chromatographic purification using a reverse phase support, (C18 silica prepared according to Journal of Organic Chemistry, 48, 1983, page 3589) and 30% CH3OH/H2O as the eluent to yield 2.3 g (72% yield) of a magenta powder, tris(3-sulfopropyl) rhodamine, represented by the formula The structure of the product was confirmed by a 300 MHz NMR spectrum.

The tris(3-sulfopropyl) rhodamine (2.3 g) was stirred in 30 ml of aqueous 1N NaOH for 1 hour under nitrogen. To this solution there was added 30 ml of 1N HCl and the solvent then evaporated to dryness under high vacuum. The resulting solid was dissolved in a small volume of water and applied to a pad of C18 silica. The salts were removed by washing with water. The desired bis (3-sulfopropyl) rhodamine carboxylic acid was removed from the pad by elution with CH3OH, the solvent removed by evaporation under vacuum and the solid product triturated with CH3CN followed by drying under vacuum to give 1.67 g (86% yield) of bis (3-sulfopropyl) rhodamine carboxylic acid*, a purple powder represented by the formula

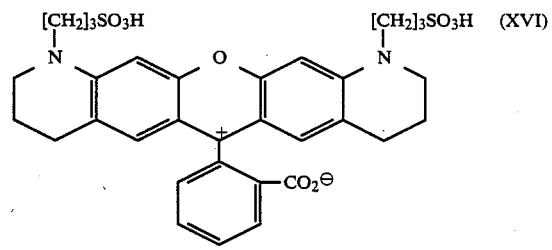

*The compound is hygroscopic and should be stored under nitrogen.

Bis (3-sulfopropyl) rhodamine carboxylic acid (50 mg, 7.67×10−5 mole) was added to a flamed/N2 cooled round bottom flask together with 2–3 ml of dry DMF and stirred at ambient temperature under nitrogen. Triethylamine (64 μl, 46.4 mg, 4.6×10−4 mole) was added followed by pivaloyl chloride (28.2 μl, 27.6 mg, 2.3×10−4 mole) and the mixture stirred for 2 hours. The reaction was monitored by TLC using a piperidine quench on aliquots. Piperazine (66 mg, 7.67×10−4 mole) was added to the formed mixed anhydride and the reaction mixture stirred for an additional 14 hours. The solvent was then removed under high vacuum and the crude mixture was purified on a silica gel column using C18 silica with 30% CH3OH/H2O as the eluent to give bis (3-sulfopropyl) rhodamine piperazinamide, represented by the formula

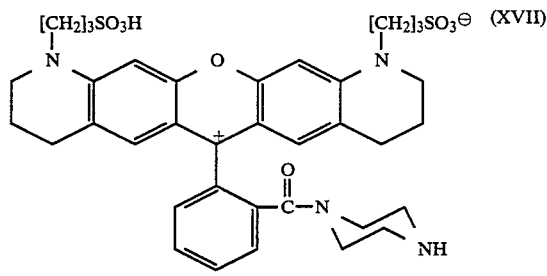

The structure of the product was confirmed by NMR spectral data (300 MHz). Quantitative analysis was consistent with a hexahydrate. The product deliquesces readily and should be stored under high vacuum or nitrogen.

The mixed anhydride of 3-(carboxylpropyl) theophylline (which was prepared following the procedure described in Jour. of Org. Chem., 45 (9) 1980, page 1711) was formed in a flamed/$N_2$ cooled round bottom flask under nitrogen by addition of pivaloyl chloride (14.5 μl, 14.5 mg, $1.20 \times 10^{-4}$ mole) and triethylamine (16.7 μl, 12.1 mg, $1.20 \times 10^{-4}$ mole) to 3-(carboxypropyl) theophylline (28.6 mg, $1.20 \times 10^{-4}$ mole) in 6 ml of dry DMF at 0° C. The mixture was stirred for 1½ hours at 0° C. and then transferred to a separate flamed/$N_2$ cooled round bottom flask containing bis (3-sulfopropyl) rhodamine piperazinamide (43.4 mg, $6.01 \times 10^{-5}$ mole) under nitrogen. The reaction mixture was stirred for 12 hours at ambient temperature. Thin layer chromatography showed an incomplete reaction so 2 more equivalents of the mixed anhydride were added to the reaction mixture. The solvent was removed under high vacuum and the crude product was purified by chromatography in accordance with the procedure previously described using 40% $CH_3OH/H_2O$ as the eluent to give 40 mg (68.7% yield) of the rhodamine/3-(carboxypropyl) theophylline conjugate represented by the formula

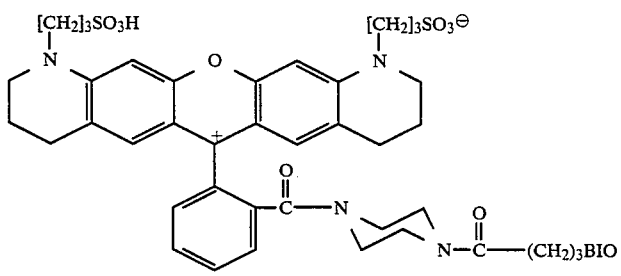

where BIO is

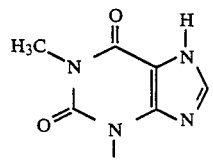

The structure of the product was confirmed by a 300 MHz NMR spectrum, m/e=958 FAB +.

EXAMPLE IV

L - thyroxine sodium salt, from Cal Biochem, (200 mg, 0.25 mmole) was added to a stirred solution of acetic anhydride (24 μl, 0.25 mmole) in 2 ml DMF at room temperature under nitrogen. Triethylamine (35 μl, 0.25 mmole) was then added and the resulting mixture stirred overnight. The solvent was removed under high vacuum, the residue taken up in 2 ml $CH_3OH$ and then 1N HCl added dropwise, with stirring, to form a white precipitate. The supernatent liquid was decanted and the solid dried under vacuum to give 180 mg (88% yield) of

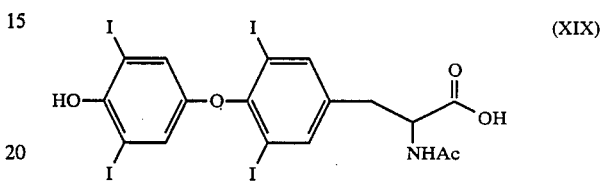

$^1$H NMR ($CD_3OD$-$CDCl_3$): 2.02 (s, 3H), 2.8–3.2 (m, 2H), 4.70 (b.t., 1H, J=7 Hz), 7.1 (s, 2H), 7.7 (s, 2H); M.S. (M$^+$819).

Trimethylacetyl chloride (30 μl, 0.24 mmole) was added dropwise to a stirred solution of 180 mg (0.22 mmole) of XIX and triethylamine (34 μl, 0.24 mmole) in 2 ml DMF at 0°–5° C. The resulting mixture was stirred under nitrogen for 1 hour and then added dropwise to a cold solution of 95 mg (1.10 mmole) piperazine in 1 ml DMF. The mixture was warmed to room temperature, stirred for 2 hours and then evaporated to dryness. The residue was triturated with $CH_3OH$, filtered, triturated with $H_2O$, filtered and dried to give 41 mg (21% yield) of

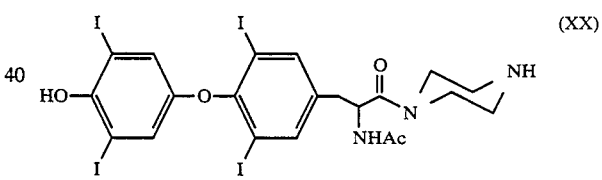

M.S. (M$^+$887).

A mixture of IX (41 mg, 0.064 mmole) and 57 mg of XX (0.064 mmole) in 1 ml DMF, at −30° C. under nitrogen, was treated in one portion with 18 μl (0.083 mmole) of diphenylphosphoryl azide. The resultant mixture was allowed to warm to room temperature and stirred overnight. The volatile matter was removed under high vacuum and the residue chromatographed on silica gel with 10% AcOH/20% CH$_3$OH/CH$_2$Cl$_2$ to give 12 mg (13% yield) of

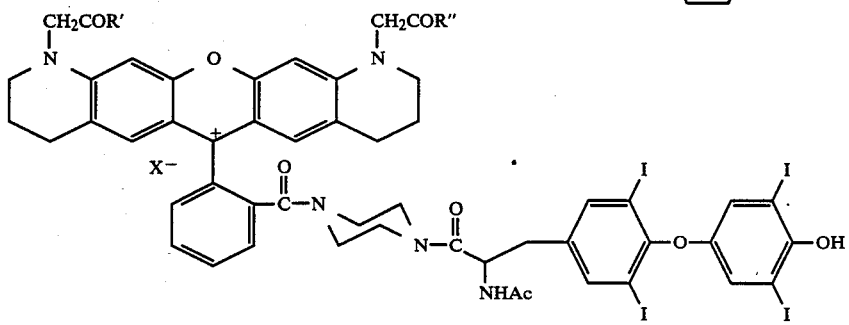

(XXI)

conjugate XXII (XXI) where R'=R" and each is —OC(CH$_3$)$_3$ and X is diphenylphosphate).

Conjugate XXIII (XXI where R' is —OH and R" is O⊖) was made from XXII following the same procedure used for XII

EXAMPLE V 1-(carboxyethyl)phenobarbital (50 mg, 1.64×10$^{-4}$ mole) was dissolved in 2 ml of dry DMF with stirring under N$_2$. The solution was cooled in an ice water bath and triethylamine (25 μl, 1.75×10$^{-4}$ mole) added in one portion. Pivaloyl chloride (22 μl, 1.75×10$^{-4}$ mole) was added to the mixture in one portion. Within several minutes a precipitate was observed and the mixture was stirred at 5° C. for 1 hour. The mixture was then added slowly, dropwise, to a solution of piperazine (70.6 mg, 8.20×10$^{-4}$ mole) in 5 ml of dry DMF with stirring under N$_2$. The reaction mixture was stirred with cooling in an ice water bath for 1 hour and then at room temperature for 1 hour followed by concentration of the solvent under high vacuum at room temperature. The semi-solid residue was charged onto a silica gel column and eluted with 10% CH$_3$OH/1% NH$_4$OH/CH$_2$Cl$_2$. The desired product fractions were concentrated under vacuum to give 45.1 mg (74% yield) of

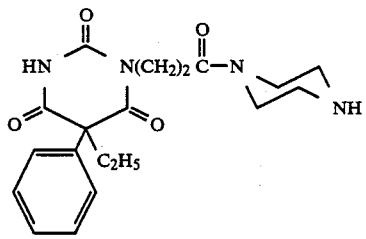

(XXIV)

Triethylamine (19 μl, 1.33×10$^{-4}$ mole) was added in one portion to a cooled solution (∼ 3° C.) of 78 mg (1.21 ×10$^{-4}$ mole) of IX in 2 ml of dry DMF. Pivaloyl chloride (17 μl, 1.33×10$^{-4}$ mole) was added to the solution in one portion with cooling. A precipitate was observed almost immediately and the mixture was stirred for 1 hour at reduced temperature. The mixture was then added quickly, dropwise, to a solution of 45 mg (1.21×10$^{-4}$ mole) of XXIV and triethylamine (19 μl, 1.33×10$^{-4}$ mole) in 2 ml of dry DMF. The resulting solution was stirred for 1 hour at reduced temperature and 1 hour at room temperature. The solution was then concentrated to a solid under high vacuum. The solid was purified on a silica gel column by eluting with 1:1 ethyl acetate/acetone to give the unreacted dye (24 mg, 31%). Elution with 10% CH$_3$OH/CH$_2$Cl$_2$ gave 65.3 mg (54.3%) of

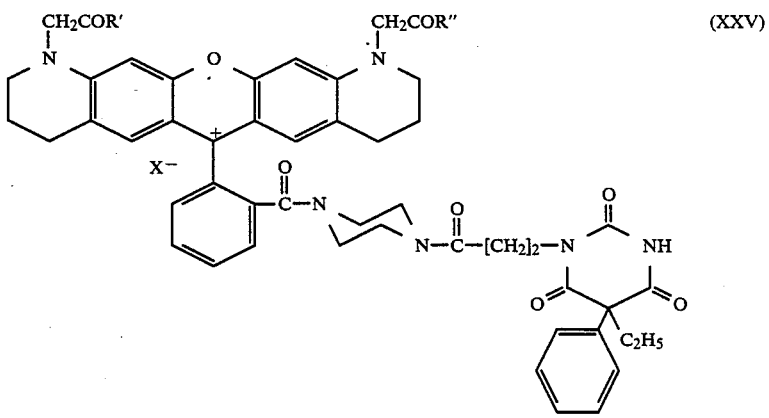

XXVI (XXV where R'=R" and each is —OC(CH$_3$)$_3$) and X is chloride).

Compound XXVI (65.3 mg, 6.57×10$^{-5}$ mole) was stirred in 1.5 ml of trifluoroacetic acid at room temperature under nitrogen for 1½ hours and the solvent then concentrated under vacuum. The residue was charged onto reverse phase silica gel and eluted with 40%

CH₃OH/H₂O and then with 60% CH₃OH/H₂O to give numerous fractions with mixtures of products. The fractions exhibiting R_f=0.79 with reverse phase silica gel were concentrated under vacuum and dried to give 6.1 mg of XXVII (XXV where R' is —OH and R" is —O⊖). Subsequent syntheses indicated that elution from normal phase silica gel with 10% CH₃OH/10% HOAc/CH₂Cl₂ provides better recovery.

EXAMPLE VI

A flask containing 40 ml of glacial acetic acid was cooled in a cold water bath and 1.9 g (0.03 mole) of sodium cyanoborohydride was added portionwise with stirring and constant cooling. After H₂ evolution had ceased, 1.0 g (0.0075 mole) of 4-hydroxyindole was added and the resulting solution was stirred at room temperature for 3 hours.

The reaction mixture was then slowly poured into a stirred solution of 50 g sodium carbonate in 400 ml H₂O. The crude product was extracted out with ethyl acetate. The solvents were removed on the rotary evaporator and the residue was chromatographed on silica gel (10% EtOAc/CH₂Cl₂) to yield 723 mg (71%) of

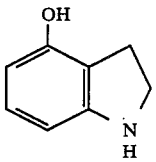

(XXVIII)

4-hydroxyindoline (XXVIII) as a white powder.

¹H NMR (CDCl₃): δ 2.83 (t, 2H), 3.43 (t, 2H), 5.13 (b.s., 1H), 5.9–6.1 (m, 2H), 6.77 (t, 1H), 8.80 (s, 1H) m/e=135.

A suspension of 1.6 g (12.1 mmole) of mono-methyl-succinate in 20 ml of dry toluene was stirred at room temperature and 140 mg (3.7 mmole) of sodium borohydride was added. No evolution of gas was observed. The suspension was treated with 100 mg (0.74 mmole) of XXVIII and the temperature of the reaction mixture was slowly raised to 60° C., during which time gas evolution started and total solution was achieved.

After 2 hours at 60°, the reaction solution was cooled to room temperature, then quenched into 200 ml saline, and the product was extracted out with EtOAc. The solvents were removed on the rotary evaporator to give a crude product which was chromatographed on silica gel (5% EtOAc/CH₂Cl₂). The product containing fractions were combined and evaporated, leaving a white solid. This solid was dissolved in CH₂Cl₂ and washed with 5% sodium bicarbonate solution. The layer was dried over sodium sulfate and then evaporated to yield 35 mg (20%) of XXIX as a pale oil.

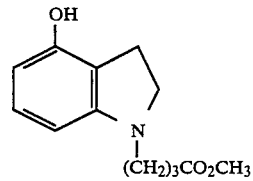

(XXIX)

¹H NMR (CDCl₃): δ 1.89 (q, 2H), 2.39 (t, 2H), 2.75 –3.2 (m, 4H), 3.37 (t, 2H), 3.63 (s, 3H) 5.95–6.15 (m, 2H), 6.88 (t, 1H) m/e=236 (FAB+).

Compound XXIX (32 mg, 0.14 mmole) was combined neat in a dry flask with phthalic anhydride (20.1 mg, 0.14 mmole) and fused ZnCl₂ (9 mg, 0.07 mmole) and the resulting mixture was heated in an oil bath at 150° C. under nitrogen for two hours. The resulting red mass was cooled to room temperature, then chromatographed on silica gel, using 3% MeOH - 5% MeOH/CH₂Cl₂ as eluant. The product containing fractions were combined and evaporated to yield 18 mg (45%) of XXX as a purple solid.

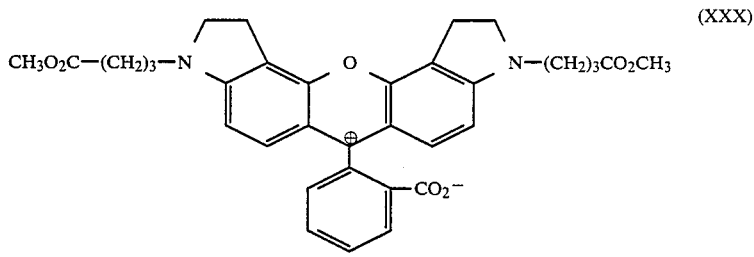

(XXX)

¹H NMR (CDCl₃+CD₃OD): δ 1.97 (m, 4H), 2.40 (t, 4H), 3.3–3.7 (m, 8H), 3.63 (s, 6H), 4.03 (t, 4H), 6.57 (d, 2H, J=9 Hz), 7.02 (d, 2H, J=9 Hz), 7.3 (m, 1H), 7.75 (m, 2H), 8.3 (m, 1H). m/e=583

A mixture of 18 mg (0.031 mmole) of XXX and 10.3 mg (0.031 mmole) of compound X in 1.5 ml DMF was cooled to −30° C. Diphenylphosphoryl azide (10 mg, 0.036 mmole) was added to the stirred solution under nitrogen and the reaction mixture was slowly allowed to warm to ambient temperature, then stirred for 60 hours. The solvents were removed under high vacuum and the purple residue was chromatographed on silica gel (5% MeOH - 15% MeOH/CH₂Cl₂) to yield 32 mg (91%) of XXXI as a purple solid.

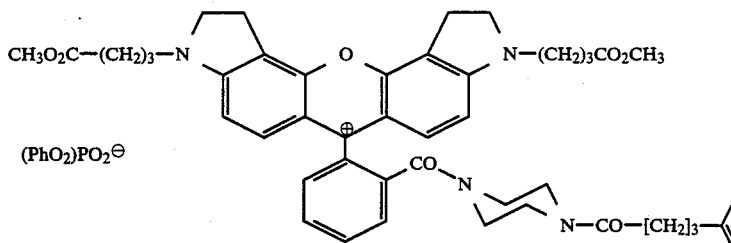
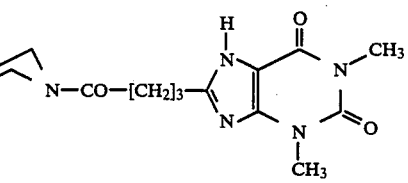

(XXXI)

¹H NMR (CDCl₃+CD₃OD) was complex but consistent with the structure of the product.

A solution of 30 mg (0.026 mmole) of XXXI in 2 ml ethanol was treated dropwise with 1.0 ml of 0.1 N NaOH solution and the resulting solution was heated at 30° C. under nitrogen until TLC showed complete hydrolysis (about 2 hours). The excess solvents were removed under high vacuum. The residue was stirred with 5% HOAc solution, and the excess solvents were again removed under vacuum. The crude product was purified by chromatography on silica gel with 10%–20% MeOH/5% HOAc/CH₂Cl₂ as the eluant to yield 14 mg (62%) of the conjugate XXXII as a purple powder.

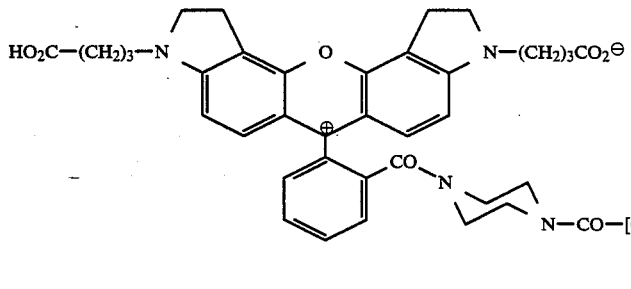
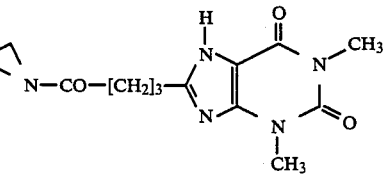

m/e=872 (FAB+).

Visible spectrum: λ $_{max}$ (pH 7 buffer): 600 nm, ε=58000.

¹H NMR (CD₃OD+CDCl₃) was complex but consistent with the counterion being internal carboxylate compensated.

EXAMPLE VII

To further illustrate the utility of the biological fluorescent conjugates of the invention a thyroxine (T4) immunoassay was carried out. The following reagents were used in the assay:

Reagent A solution: 50 mmoles HEPES buffer (pH 7.2); 10 mmoles Na₂ EDTA; 0.02% 8-anilino-naphthalene sulfonate (ANS); 0.1% bovine serum albumin (BSA); and 0.05% NaN₃.

Reagent B solution: reagent A and 5% polyethylene glycol (PEG; NW 6000).

Calibrator solutions were made having 1, 25, 50, 100, 200 and 400 ng T4/µl of Reagent, A, respectively. The calibrator solutions (200 µl) were each combined with 200 µl of mouse monoclonal anti-T4 antibody (Behringwerke AG 49/7), 0.15 mmole Ig G, in Reagent A and 200 µl of a solution of conjugate, 0.17 mmole, in Reagent A. The mixture was incubated for 60 minutes at room temperature. Subsequently, 200 µl of 2% mouse normal serum in Reagent B and 200 µl of goat anti-mouse Ig G antibody (1/16 dilution of Calbiochem Cat. No. 401210) in Reagent B were added and the mixture further incubated for 15 minutes at room temperature.

The mixtures were then centrifuged for 15 minutes at 3000 g and the supernatant liquid decanted. The fluorescence of the free conjugate in the supernatant liquid was measured on a Perkin Elmer MPF 44 Fluorophotometer with excitation at 565 nm and the emmission at 590 nm measured. Table I shows the results obtained:

TABLE I

| Thyroxin (ng/µl) | Free Conjugate (%) |
|---|---|
| 1 | 19.0 |
| 25 | 25.4 |
| 50 | 39.8 |
| 100 | 71.8 |
| 200 | 84.2 |
| 400 | 87.0 |

The standard curve exhibited good dose response in the 70–110 ng T4/ml range of interest.

Although the invention has been described with respect to specific preferred embodiments, it is not intended to be limited thereto but rather those skilled in the art will recognize that variations and modifications may be made therein which are within the spirit of the invention and the scope of the appended claims. For example, the rings of the rhodamine label moiety of the conjugates can be appropriately substituted further such as with the solubilizing groups disclosed. Thus, analogs possessing the advantageous features of the conjugates of the present invention will be considered as equivalents thereof for the purposes of the claims herein.

What is claimed is:

1. A fluorescent diagnostic assay comprising combining in an assay medium: a sample suspected of containing an analyte; a binding partner for said analyte; and a conjugate of said analyte or an analogue thereof and a fluorescent compound, said conjugate represented by the formula $$\left[ R-N \underset{Y_n}{\overset{X_m}{\underset{\phantom{X}}{\bigg\langle}}} \underset{\phantom{X}}{\overset{O}{\bigotimes}} \underset{Z_q}{\overset{W_p}{\underset{\phantom{X}}{\bigg\rangle}}} N-R_1 \right]_{(A)_x}$$

with $R_2$, $R_3$ substituents on phenyl wherein

W, X, Y and Z each independently is $-(CH_2)_a(CHR_4)(CH_2)_b-$;

R, $R_1$, $R_3$ and $R_4$ each independently is hydrogen, a hydrophilic group or a substituent including said analyte or an analogue thereof;

$R_2$ is $-CO_2^{\ominus}$, $SO_3^{\ominus}$ or a substituent including said analyte or an analogue thereof;

provided that one of R, $R_1$, $R_2$, $R_3$ and $R_4$ is a substituent including said analyte or an analogue thereof and at least one of the remaining of R, $R_1$, $R_3$ and $R_4$ is a hydrophilic group;

a and b each independently is an integer of from 0 to 4, provided that the sum of a+b is an integer of from 1 to 4;

m and n each is 0 to 1 provided that one of m and n is 0 and the other is 1;

p and q each is 0 or 1 provided that one of p and q is 0 and the other is 1;

A is a counterion or the counterions to balance the overall charges on the conjugate moiety; and x is 0 or 1;

separating bound conjugate from free conjugate;

measuring the level of the fluorescent signal of said bound or free conjugate; and relating said level of said signal to the amount of said analyte in said sample.

2. The assay as defined in claim 1 wherein said conjugate is represented by the formula

[structure with $R_{12}$, $R_{13}$, $R_{14}$, $R_{15}$, $R_2$, $R_3$ substituents] $(A)_x$ where $R_{12}$, $R_{13}$, $R_{14}$ and $R_{15}$ each independently is hydrogen, a hydrophilic group or a substituent including said analyte or an analogue thereof, provided that one of $R_2$, $R_3$, $R_{12}$, $R_{13}$, $R_{14}$ and $R_{15}$ is a substituent including said analyte or an analogue thereof and at least one of the remaining of $R_3$, $R_{12}$, $R_{13}$, $R_{14}$ and $R_{15}$ is a hydrophilic group.

3. The assay as defined in claim 2 wherein $R_2$ is a substituent including said analyte or an analogue thereof.

4. The assay as defined in claim 3 wherein $R_{12}$ is a hydrophilic group.

5. The assay as defined in claim 4 wherein $R_{13}$ is a hydrophilic group.

6. The assay as defined in any of claims 4 and 5 wherein said hydrophilic group is a carboxylic acid, a polyether, a polyalcohol, an amine, a sulfonic acid, a phosphonic acid, a phosphonic ester, a phosphate, a phosphate ester, a phosphinic acid, a boronic acid or a borinic acid.

7. The assay as defined in claim 1 wherein said conjugate is represented by the formula

[structure with $R_{12}$, $R_{13}$, $R_{14}$, $R_{15}$, $R_2$, $R_3$ substituents] $(A)_x$ wherein $R_{12}$, $R_{13}$, $R_{14}$ and $R_{15}$ each independently is hydrogen, a hydrophilic group or a substituent including said analyte or an analogue thereof, provided that one of $R_2$, $R_3$, $R_{12}$, $R_{13}$, $R_{14}$ and $R_{15}$ is a substituent including said analyte or an analogue thereof and at least one of the remaining of $R_3$, $R_{12}$, $R_{13}$, $R_{14}$ and $R_{15}$ is a hydrophilic group.

8. The assay as defined in claim 7 wherein $R_2$ is a substituent including said analyte or an analogue thereof.

9. The assay as defined in claim 8 wherein $R_{12}$ is a hydrophilic group.

10. The assay as defined in claim 9 wherein $R_{13}$ is a hydrophilic group.

11. The assay as defined in any of claims 9 and 10 wherein said hydrophilic group is a carboxylic acid, a polyether, a polyalcohol, an amine, a sulfonic acid, a phosphonic acid, a phosphonic ester, a phosphate, a phosphate ester, a phosphinic acid, a boronic acid or a borinic acid.

12. A diagnostic assay element adapted to receive a sample of a biological fluid and to provide a detectable signal as a function of an analyte which may be present in said fluid, said assay element including a fluorescent conjugate represented by the formula $$\left[ R-N \underset{Y_n}{\overset{X_m}{\underset{\phantom{X}}{\bigg\langle}}} \underset{\phantom{X}}{\overset{O}{\bigotimes}} \underset{Z_q}{\overset{W_p}{\underset{\phantom{X}}{\bigg\rangle}}} N-R_1 \right]_{(A)_x}$$

with $R_2$, $R_3$ substituents on phenyl wherein

W, X, Y and Z each independently is —(—CH$_2$)$_a$(CHR$_4$)(CH$_2$—)$_b$;

R, R$_1$, R$_3$ and R$_4$ each independently is hydrogen, a hydrophilic group or a substituent including a biologically active moiety selected from the group consisting of an antigen, an antibody, a hapten, an Fab fragment and a DNA probe, wherein said biologically active moiety is an analyte of interest, an analogue thereof or a binding partner of said analyte;

R$_2$ is —CO$_2$⊖, SO$_3$⊖ or a substituent including said biologically active moiety;

provided that one of R, R$_1$, R$_2$, R$_3$ and R$_4$ is a substituent including said biologically active moiety and at least one of the remaining of R, R$_1$, R$_3$ and R$_4$ is a hydrophilic group;

a and b each independently is an integer of from 0 to 4, provided that the sum of a+b is an integer of from 1 to 4;

m and n each is 0 to 1 provided that one of m and n is 0 and the other is 1;

p and q each is 0 or 1 provided that one of p and q is 0 and the other is 1;

A is a counterion or the counterions to balance the overall charges on the conjugate moiety; and x is 0 or 1.

13. The diagnostic element as defined in claim 12 which includes a support carrying at least one reagent layer.

14. The diagnostic element as defined in claim 12 which includes the binding partner of said biologically active moiety present in said conjugate.

15. The assay element as defined in claim 12 wherein said conjugate is represented by the formula

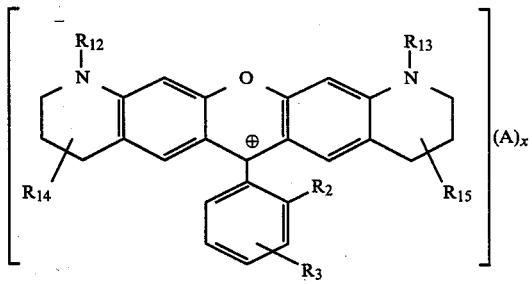

wherein R$_{12}$, R$_{13}$, R$_{14}$ and R$_{15}$ each independently is hydrogen, a hydrophilic group or a substituent including said biologically active moiety, provided that one of R$_2$, R$_3$, R$_{12}$, R$_{13}$, R$_{14}$ and R$_{15}$ is a substituent including said biologically active moiety and at least one of the remaining of R$_3$, R$_{12}$, R$_{13}$, R$_{14}$ and R$_{15}$ is a hydrophilic group.

16. The assay element as defined in claim 15 wherein R$_2$ is a substituent including said biologically active moiety.

17. The assay element as defined in claim 16 wherein R$_{12}$ is a hydrophilic group.

18. The assay element as defined in claim 17 wherein R$_{13}$ is a hydrophilic group.

19. The assay element as defined in any of claims 17 or 18 wherin said hydrophilic group is a carboxylic acid, a polyether, a polyalcohol, an amine, a sulfonic acid, a phosphonic acid, a phosphonic ester, a phosphate, a phosphate ester, a phosphinic acid, a boronic acid or a borinic acid.

20. The assay element as defined in claim 12 wherein said conjugate is represented by the formula

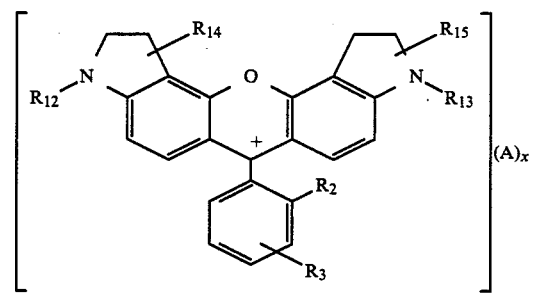

wherein R$_{12}$, R$_{13}$, R$_{14}$ and R$_{15}$ each independently is hydrogen, a hydrophilic group or a substituent including said biologically active moiety, provided that one of R$_2$, R$_3$, R$_{12}$, R$_{13}$, R$_{14}$ and R$_{15}$ is a substituent including said biologically active moiety and at least one of the remaining of R$_3$, R$_{12}$, R$_{13}$, R$_{14}$ and R$_{15}$ is a hydrophilic group.

21. The assay element as defined in claim 20 wherein R$_2$ is a substituent including said biologically active moiety.

22. The assay element as defined in claim 21 wherein R$_{12}$ is a hydrophilic group.

23. The assay element as defined in claim 22 wherein R$_{13}$ is a hydrophilic group.

24. The assay element as defined in any of claims 22 or 23 wherein said hydrophilic group is a carboxylic acid, a polyether, a polyalcohol, an amine, a sulfonic acid, a phosphonic acid, a phosphonic ester, a phosphate, a phosphate ester, a phosphinic acid, a boronic acid or a borinic acid.

25. A fluorescent conjugate represented by the formula

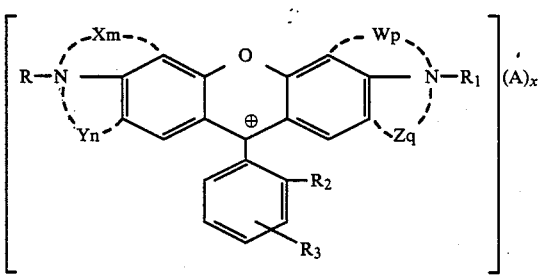

wherein

W, X, Y and Z each independently is —(—CH$_2$)$_a$(CHR$_4$)(CH$_2$—)$_b$;

R, R$_1$, R$_3$ and R$_4$ each independently is hydrogen, a hydrophilic group or a substituent including a biologically active moiety selected from the group consisting of an antigen, an antibody, a hapten, an Fab fragment and a DNA probe;

R$_2$ is —CO$_2$⊖, SO$_3$⊖ or a substituent including said biologically active moiety;

provided that one of R, R$_1$, R$_2$, R$_3$ and R$_4$ is a substituent including said biologically active moiety and at least one of the remaining of R, R$_1$, R$_3$ and R$_4$ is a hydrophilic group;

a and b each independently is an integer of from 0 to 4, provided that the sum of a+b is an integer of from 1 to 4;

m and n each is 0 to 1 provided that one of m and n is 0 and the other is 1;

p and q each is 0 or 1 provided that one of p and q is 0 and the other is 1;

A is a counterion or the counterions to balance the overall charges on the conjugate moiety; and x is 0 or 1.

26. The fluorescent conjugate as defined in claim 25 which is represented by the formula

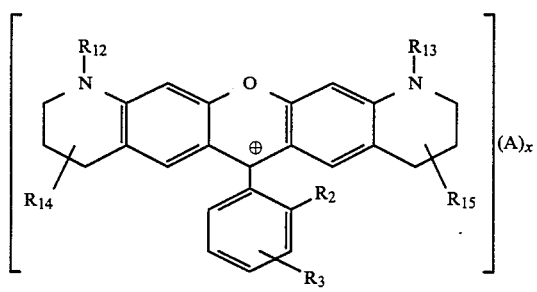

wherein $R_{12}$, $R_{13}$, $R_{14}$ and $R_{15}$ each independently is hydrogen, a hydrophilic group or a substituent including said biologically active moiety, provided that one of $R_2$, $R_3$, $R_{12}$, $R_{13}$, $R_{14}$ and $R_{15}$ is a substituent including said biologically active moiety and at least one of the remaining of $R_3$, $R_{12}$, $R_{13}$, $R_{14}$ and $R_{15}$ is a hydrophilic group.

27. The fluorescent conjugate as defined in claim 26 wherein $R_2$ is a substituent including said biologically active moiety.

28. The fluorescent conjugate as defined in claim 25 which is represented by the formula

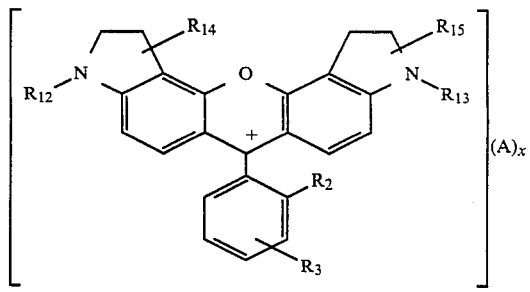

wherein $R_{12}$, $R_{13}$, $R_{14}$ and $R_{15}$ each independently is hydrogen, a hydrophilic group or a substituent including said biologically active moiety, provided that one of $R_2$, $R_3$, $R_{12}$, $R_{13}$, $R_{14}$ and $R_{15}$ is a substituent including said biologically active moiety and at least one of the remaining of $R_3$, $R_{12}$, $R_{13}$, $R_{14}$ and $R_{15}$ is a hydrophilic group.

29. The fluorescent conjugate as defined in claim 28 wherein $R_2$ is a substituent including said biologically active moiety.

30. The fluorescent conjugate as defined in claim 25 wherein said hydrophilic group is a carboxylic acid, a polyether, a polyalcohol, an amine, a sulfonic acid, a phosphonic acid, a phosphonic ester, a phosphate, a phosphate ester, a phosphinic acid, a boronic acid or a borinic acid.

* * * * *

UNITED STATES PATENT AND TRADEMARK OFFICE
CERTIFICATE OF CORRECTION

PATENT NO. : 4,900,686

DATED : February 13, 1990

INVENTOR(S) : Michael J. Arnost et al

It is certified that error appears in the above-identified patent and that said Letters Patent is hereby corrected as shown below:

Column 19, in claim 1, delete the formula and replace it with the following.

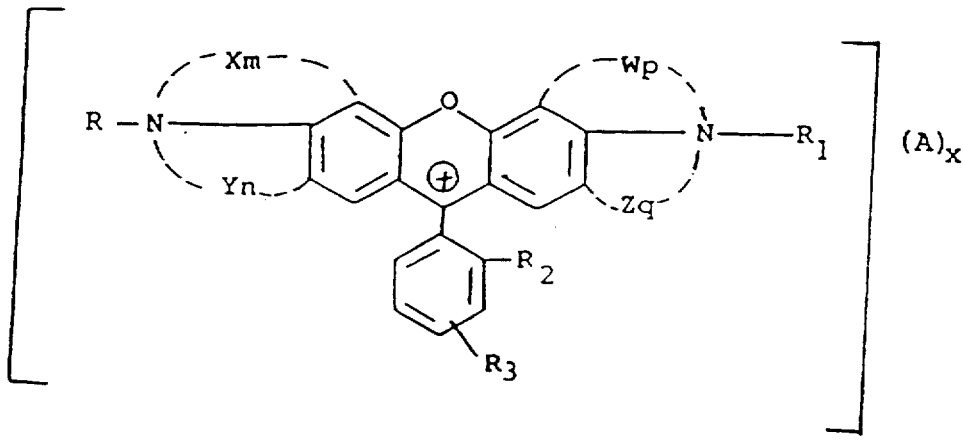

Signed and Sealed this

Fifth Day of March, 1991

Attest:

HARRY F. MANBECK, JR.

Attesting Officer

Commissioner of Patents and Trademarks